United States Patent
Franzen et al.

(10) Patent No.: US 7,504,640 B2
(45) Date of Patent: Mar. 17, 2009

(54) IONIZATION OF DESORBED MOLECULES

(75) Inventors: Jochen Franzen, Bremen (DE); Karsten Michelmann, Harpstedt (DE)

(73) Assignee: Bruker Daltonik, GmbH, Bremen (DE)

( * ) Notice: Subject to any disclaimer, the term of this patent is extended or adjusted under 35 U.S.C. 154(b) by 236 days.

(21) Appl. No.: 11/522,112

(22) Filed: Sep. 15, 2006

(65) Prior Publication Data
US 2009/0039283 A1 Feb. 12, 2009

(30) Foreign Application Priority Data
Sep. 16, 2005 (DE) .................. 10 2005 044 307

(51) Int. Cl.
- H01J 27/00 (2006.01)
- H01J 49/04 (2006.01)
- B01D 59/44 (2006.01)

(52) U.S. Cl. .................. 250/425; 250/281; 250/282; 250/288; 250/423 R

(58) Field of Classification Search ........... 250/281, 250/282, 288, 423 R, 424, 425
See application file for complete search history.

(56) References Cited

U.S. PATENT DOCUMENTS

| | | | | |
|---|---|---|---|---|
| 3,555,272 | A * | 1/1971 | Munson | 250/424 |
| 4,156,814 | A * | 5/1979 | Hunt et al. | 250/423 P |
| 4,175,234 | A * | 11/1979 | Hunt et al. | 250/427 |
| 5,015,862 | A * | 5/1991 | Holmes et al. | 250/423 R |
| 5,663,561 | A * | 9/1997 | Franzen et al. | 250/288 |
| 6,515,280 | B1 * | 2/2003 | Baykut | 250/288 |
| 6,528,320 | B2 * | 3/2003 | Hutchens et al. | 436/173 |
| 6,707,031 | B1 * | 3/2004 | Weinberger et al. | 250/281 |
| 6,777,671 | B2 * | 8/2004 | Doroshenko | 250/287 |
| 6,989,528 | B2 * | 1/2006 | Schultz et al. | 250/281 |
| 7,022,981 | B2 * | 4/2006 | Kato | 250/288 |
| 7,196,326 | B2 * | 3/2007 | Franzen et al. | 250/288 |
| 2002/0079443 | A1 * | 6/2002 | Krutchinsky et al. | 250/281 |
| 2002/0145109 | A1 * | 10/2002 | Doroshenko | 250/287 |

(Continued)

FOREIGN PATENT DOCUMENTS

DE 196 08 963 A1 10/1996

(Continued)

OTHER PUBLICATIONS

Krutchinsky, Andrew, et al., "Orthogonal Injection of Matrix-Assisted Laser Desorption/Ionization Ions Into a Time-of-Flight Spectrometer Through a Collisional Damping linterface", Rapid Communications in Mass Spectrometry, 1998, pp. 508-518, vol. 12, Issue 9, John Wiley & Sons, Ltd.

Primary Examiner—David A. Vanore
Assistant Examiner—Bernard E Souw
(74) Attorney, Agent, or Firm—Law Offices of Paul E. Kudirka

(57) ABSTRACT

An ion source generates ions from analyte molecules which are desorbed from a sample on the surface of a sample support in a pressure range of approximately 30 to 300 pascal. Reactant ions are generated in a separate ion source and guided by ion guides to the point in front of the sample or to a reaction chamber in which the desorbed molecules are located. The reactant ions ionize the desorbed molecules to form analyte ions. The analyte molecules can be mixed in matrix material or adsorbed on the sample support surface without additives. The desorption can be continuous or pulsed, for example by light from lasers or diodes.

19 Claims, 4 Drawing Sheets

U.S. PATENT DOCUMENTS

| | | | |
|---|---|---|---|
| 2002/0155620 A1* | 10/2002 | Hutchens et al. | 436/173 |
| 2003/0098413 A1* | 5/2003 | Weinberger et al. | 250/288 |
| 2004/0089804 A1* | 5/2004 | Dantus et al. | 250/288 |
| 2004/0183007 A1* | 9/2004 | Belov et al. | 250/287 |
| 2005/0112650 A1* | 5/2005 | Chang et al. | 435/6 |
| 2005/0279931 A1* | 12/2005 | Franzen et al. | 250/290 |
| 2006/0097143 A1* | 5/2006 | Franzen | 250/282 |
| 2006/0110819 A1* | 5/2006 | Lomas et al. | 435/287.2 |
| 2006/0183242 A1* | 8/2006 | Huang et al. | 436/166 |
| 2006/0186332 A1* | 8/2006 | Haase et al. | 250/288 |
| 2006/0261267 A1* | 11/2006 | Sze et al. | 250/288 |
| 2008/0054171 A1* | 3/2008 | Bonn et al. | 250/282 |

FOREIGN PATENT DOCUMENTS

| | | |
|---|---|---|
| DE | 199 11 801 C1 | 1/2001 |
| EP | 1 367 632 A2 | 12/2003 |
| EP | 1 536 452 A1 | 6/2005 |
| GB | 2310950 A | 9/1997 |
| GB | 2348049 A | 9/2000 |
| GB | 2410370 A | 7/2005 |
| WO | WO 00/77822 A2 | 12/2000 |
| WO | WO 03/052399 A2 | 6/2003 |

\* cited by examiner

IONIZATION OF DESORBED MOLECULES

FIELD OF THE INVENTION

The invention relates to the generation of ions from analyte molecules which are desorbed off the surfaces of suitable sample supports.

BACKGROUND

One important type of ionization for biomolecules is ionization by matrix-assisted laser desorption and ionization (MALDI). This process ionizes the analyte biomolecules from mixtures with molecules of a matrix substance on sample supports. The ratio of analyte molecules to matrix molecules is around one to ten thousand. Hundreds of samples can be applied to a sample support using pipetting robots which are available for this purpose. Transporting the samples on the sample support into the focus of a UV pulsed laser takes only fractions of seconds; as much time as is ever needed is available for the analysis of this sample (until the sample is completely used up). This sets MALDI very favorably apart from electrospray ionization, which provides only very slow sample changing or, in conjunction with chromatography, restricts the analysis time to the duration of the chromatographic peak. MALDI is ideal for the identification of tryptically digested proteins which have been separated by 2D gel electrophoresis. The MALDI analysis of peptides which have been separated by liquid chromatography and applied to MALDI sample supports is also gaining ground ("HPLC MALDI").

A disadvantage of MALDI, however, is that it only ionizes one ten thousandth of the analyte molecules. One attomol of an analyte substance, i.e., approx. 600,000 molecules, only produces around 60 analyte ions. The rest are not ionized; some of the remaining molecules are possibly contained in splashes of molten matrix substance and completely excluded from access to ionization, while a large proportion of the analyte molecules are simply not ionized in the laser desorption process.

Until now, matrix-assisted laser desorption has principally been carried out in high vacuum. Its starting point is a solid sample mixture prepared on a sample support. The sample consists mainly of small crystals of the matrix substance which are admixed in low proportions (only around one hundredth of one percent or less) with molecules of the analyte substance. These analyte molecules are embedded individually into the crystal lattice of the matrix crystals or are located in inter-crystal boundary surfaces. The samples prepared in this way are irradiated with short pulses of UV laser light. The duration of the pulses is roughly between two and ten nanoseconds. This produces vaporization clouds which contain both ions of the matrix substance as well as some analyte ions. Some of the analyte ions are already contained in the solid sample in ionized form, some are created directly in the explosive vaporization process in the hot plasma, and a third fraction is formed in the expanding cloud by proton transfer in reactions with the matrix ions.

Laser desorption, which was previously only used in high vacuum, has of late also been used at atmospheric pressure, simplifying the sample introduction but not, as yet, increasing the analytical sensitivity. This method is termed AP-MALDI.

This laser desorption at atmospheric pressure is characterized by the formation of a vapor cloud which arises when sample preparation material is vaporized in pulses by the laser light bombardment, and which can be entrained with the ambient gas. The vapor cloud initially consists only of matrix vapor with analyte molecules blown likewise into the gaseous phase. Only a very small fraction of the analyte molecules, in the order of one hundredth of one percent or less, are ionized. The matrix substance is similarly weakly ionized; in absolute figures, however, the matrix ions are in the majority many times over. This vapor cloud mixes in a thin boundary layer with ambient gas, but remains together for a long time. In the vapor cloud, the matrix ions can thus react further by collisions with analyte molecules, forming analyte ions. It is thus possible that more analyte ions are formed at atmospheric pressure than with MALDI in high vacuum, but this advantage is counteracted by the disadvantage that the ions from this more or less expanded vapor cloud are generated at atmospheric pressure and have to be transferred into the vacuum system of the mass spectrometer. The analyte ions which are lost as a result have, until now, been greater in number than the gain in additional analyte ions—if, indeed, this occurs at all.

A method of matrix-assisted laser desorption at atmospheric pressure has also been described in which it is not the laser desorption itself which brings about the ionization of the analyte molecules but the ionization is achieved in the subsequent ion/molecule reactions. The matrix substance thus no longer has to perform the task of ionizing the analyte molecules. For the desorption here it is possible to specifically use a substance for the matrix which decomposes into small gas molecules under laser bombardment and thus has only the three objectives of (1) binding the analyte substances firmly to the surface of the sample support, (2) absorbing the laser light, and (3) vaporizing in such a way that it decomposes, transferring the confined analyte molecules intact and isolated from each other into the gaseous phase. The chemical ionization is then undertaken, for example by forming primary ions by means of the electrons of a corona discharge (J. Franzen and C. Köster, DE 196 08 963; corresponding to GB 2 299 445 and U.S. Pat. No. 5,663,561). It is difficult to carry out the chemical ionization, however, since it is very difficult to get the gas cloud with the analyte molecules and the gas cloud with the ions for the chemical ionization to mix sufficiently intensively with each other in a short time.

The desorption of analyte molecules does not have to be carried out with laser light. It is also possible to desorb adsorbed molecules with shock waves, temperature shocks and especially with vacuum sparks, even if desorption with laser light is by far and away the easiest option.

MALDI in an ambient gas at a pressure of around 100 pascal has already been reported (A. N. Krutchinski et al., Rapid Comm. Mass Spectrom. 12, 1998, 508-518). A MALDI ion source which also operates in this pressure range but under a pressure surge of a gas introduced as pulses has been described in DE 199 11 801 C1 (G. Baykut).

Whenever the term "mass of the ions" or simply just "mass" is used here in connection with ions, it is always the "charge-related mass" m/z which is meant, i.e., the physical mass m of the ions divided by the dimensionless and absolute number z of the positive or negative elementary charges which this ion carries.

The term "desorption" here should be taken to mean all types of release of molecules from the solid phase into the gaseous phase, as is already the case with the term MALDI (matrix assisted laser desorption and ionization). It is irrelevant here whether the molecules to be desorbed are adsorbed naked on a surface or whether they are embedded in, or attached on, another material, of any type.

An "ion guide" here should be taken to mean a device by means of which ions can be intentionally transported from one location to another. This can be achieved aerodynamically or by systems of electric and magnetic electrodes or yokes, and particularly by rod systems or systems of apertured diaphragms to which the phases of an RF voltage are applied.

SUMMARY

The invention is based on a desorption of the analyte molecules in an ambient gas in a pressure range preferably between 30 and 300 pascal and on an ionization of the desorbed analyte molecules by suitable reactant ions, the reactant ions being produced in a separate reactant ion source and guided by an ion guide, either continuously or in pulses, to the location in front of the desorbing sample. In this pressure range, the desorbed analyte molecules are efficiently cooled by the ambient gas and thus kept from decomposing, on the one hand and, on the other, rapidly mixed with the reactant ions. The desorption can be continuous or pulsed. It can particularly be done by light from lasers or diodes.

The invention first desorbs the analyte molecules from the samples on the surface of a sample support at an ambient gas pressure of roughly between 30 and 300 Pascal, preferably by light from a laser or a laser diode. The optimum pressure can also lie between 10 and 1,000 Pascal, depending on the ambient gas and sample preparation. The ambient gas used can particularly be ultrapure nitrogen, helium, argon, or another low mass gas. The ambient gas should preferably be inert. If the analyte molecules on the surface of the sample support are embedded in matrix material, they are now in a cloud of desorbed sample material, otherwise they are alone in the ambient gas. In principle, the desorption can be carried out using any desorption processes other than light, but desorption using light of a suitable wavelength is a method which is well-established and easily managed and which has been proven many times over. The rapid expansion of the desorption cloud is sufficiently damped by the ambient gas, and the analyte molecules are cooled so quickly, that the majority of molecules cannot decompose. After desorption, the analyte molecules are thus unattached (not clustered together) and stable in the gaseous phase.

The invention now ionizes the analyte molecules released, preferably by proton transfer in reactions with reactant ions, as is familiar from chemical ionization. With pulsed desorption, the reactant ions are already in a dense concentration in front of the sample or, especially in the case of continuous desorption, they are blown to the desorbing cloud containing analyte molecules together with a little ambient gas, either continuously or in pulses. In the pressure range mentioned, most of the desorption cloud and the ambient gas which is fed in mix almost immediately with the reactant ions because of the free path lengths of a few hundredths to a few tenths of a millimeter. The two flows of gas molecules which meet have a very wide zone of immediate mixing, very different to that found at atmospheric pressure.

The reactant ions are generated in a separate reactant ion source, preferably at around the same pressure at which desorption also occurs, and guided in large numbers by ion guides to the point in front of the sample, before or during the desorption. It is particularly favorable if the reactant ions are produced in an ion source like the ones used for chemical ionization. In a conventional CI ion source, however, the reactant ions formed internally are brought together with analyte molecules while still in the ion source itself, and react with them by ionization, whereas the reactant ions here are extracted from the ion source. A reactant ion source of this type operates particularly well at a pressure of around 100 to 200 pascal.

If pulsed desorption is carried out, then the adiabatically expanding desorption cloud with the analyte molecules penetrates around 10 to 20 millimeters into the ambient gas with the reactant ions in around 10 to 50 microseconds; the ionization of the analyte molecules is now largely complete. The cloud of analyte ions can now be driven into an ion funnel by the application of electric DC and RF fields, the ion funnel guiding the analyte ions via further intermediate stations to a mass analyzer or to another spectrometer. The ion funnel can incorporate a diaphragm stack at its end whose special design means it forms a quadrupole field, whereby good focusing of the analyte ions for extraction by an apertured diaphragm stack designed as an ion-optical lens is achieved. In this phase of the transmission of the analyte ions, the RF voltage across the diaphragms of the ion funnel can also be set so high that the remaining reactant ions, which generally have a relatively low molecular weight, leave the system. The length of time taken by the steps necessary for expansion of the desorption cloud with reaction of the analyte molecules, expulsion of the analyte molecules from the reaction region and refilling the reaction chamber with reactant ions means that the pulse frequency is limited to between five and a maximum of ten kilohertz.

If there is continuous desorption, for example as a result of continuous decomposition of a thin layer of explosive at the focus of a laser diode, the reactant ions also are supplied continuously, or in rapid pulses. The rapid pulsing promotes rapid mixing. Here too, the analyte ions formed can be collected by an ion funnel and transmitted on. Rapid switching of voltages is not required to transport the analyte ions away. For continuous desorption it is favorable if a high migration rate of the light focus on the sample support is generated. Desorption produced by a high frequency modulated laser diode with a frequency higher than 20 kilohertz is also included here in the term "continuous desorption" since, in this case, the individual desorption clouds practically continuously merge with each other.

Figure 1:
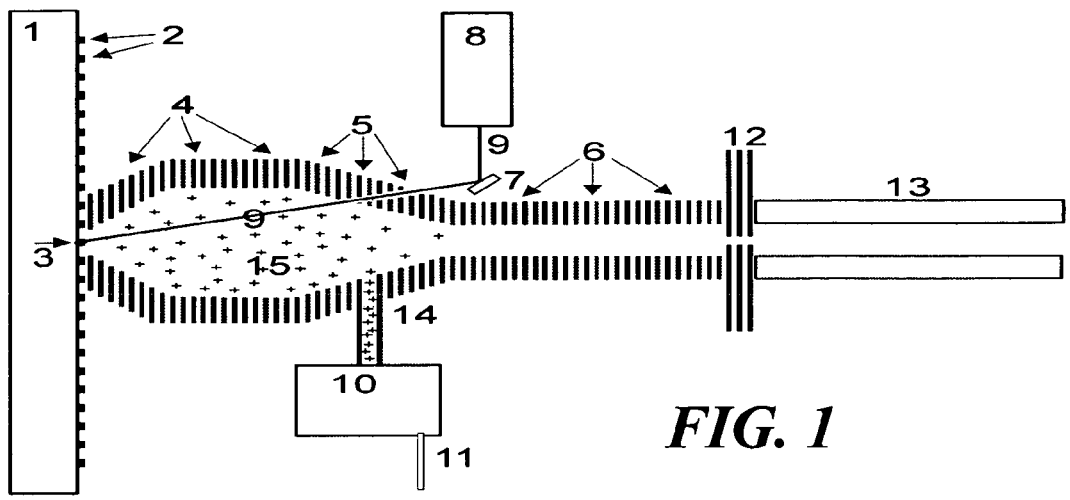
FIGS. 1 to 3 schematically illustrate three phases of the ionization of analyte molecules in a device according to this invention which operates with pulsed laser light.

The moveable sample support plate (1) carries a large number of samples (2), one of these samples (3) being at the focus of the laser beam (9) at this time. The laser beam (9) from the laser (8) is deflected via the mirror (7) onto the sample (3). The sample (3) is located at the entrance aperture of a reaction chamber (15) formed from a large number of ring diaphragms (4) and (5); the two phases of an RF voltage are applied to alternate adjacent ring diaphragms. This creates a so-called pseudopotential which repels ions and can thus confine them in the reaction chamber (15).

FIG. 1 shows this reaction chamber (15) at the time of the laser bombardment. The reaction chamber (15) is filled with reactant ions which originate from a reactant ion source (10) with gas feeder (11) and which have been guided via a small ion guide (14) into the reaction chamber (15).

Figure 2:
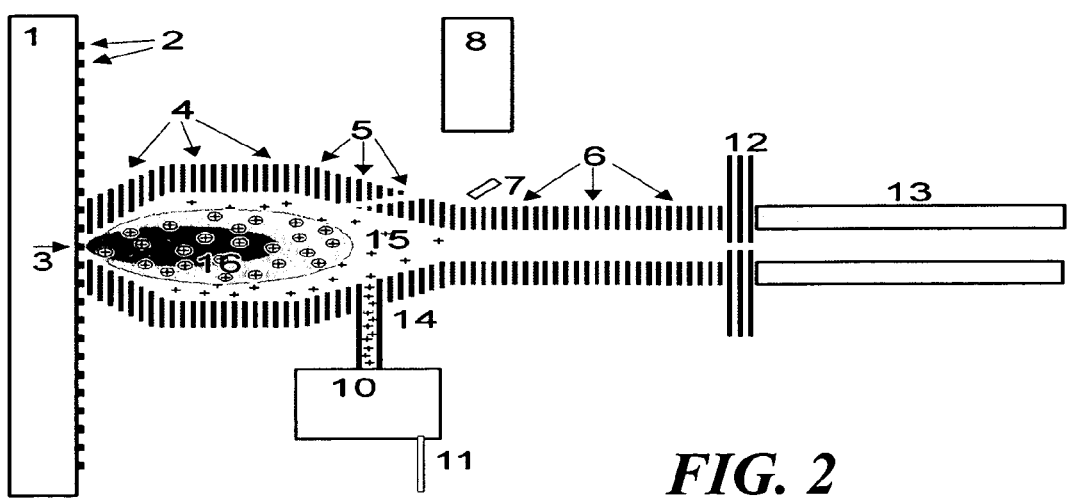

FIG. 2 shows the state some 50 microseconds after the laser bombardment. The cloud (16) with vaporized sample material has expanded; the cloud also contained the analyte molecules. A large proportion of these have been ionized by the reactant ions by proton transfer.

Figure 3:
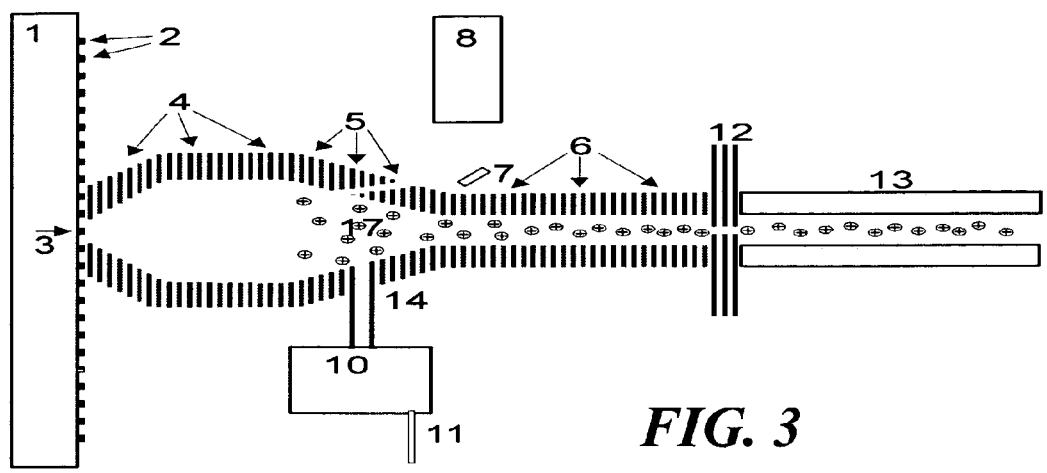

FIG. 3 illustrates how the analyte ions are now driven by a slight DC voltage gradient across the ring diaphragm systems (4) and (5), which is superimposed on the RF voltages, into the funnel-shaped part (5) of the reaction chamber and from there into the quadrupole diaphragm stack (6). In this quadrupole diaphragm stack (6) there is preferably not only a slight DC voltage drop but also a quadrupole RF field which brings the analyte ions, whose motion is damped in the ambient gas, into the axis of the diaphragm stack (6), from where they can be particularly favorably transmitted through the apertured diaphragm lens (12) into an RF ion guide (13). This ion guide (13) consists here of pole rods which are supplied with RF voltage and can bring the analyte ions into the analyzer part of a mass spectrometer (not shown here), where they can be analyzed according to their mass and intensity, for example.

Figure 4:
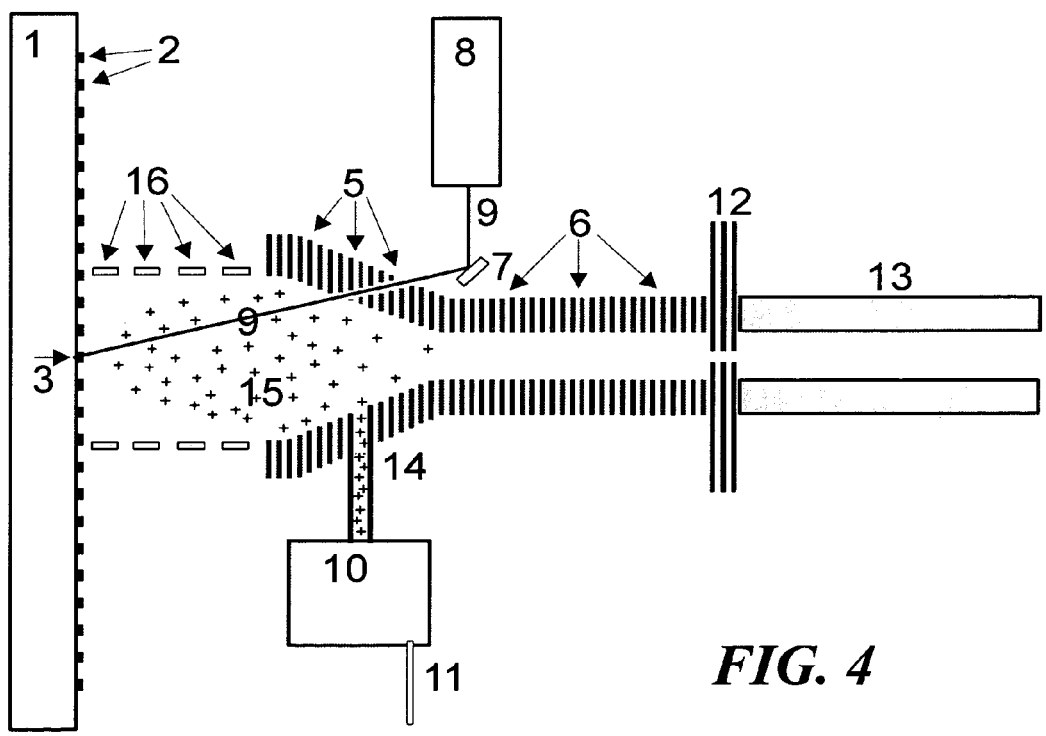

FIG. 4 illustrates a reaction chamber in front of the sample (3), the main part not being constructed of a large number of apertured diaphragms but simply of ring diaphragms (16) which carry a DC potential which repels the reactant ions. The potential on the axis of the ion funnel (5) pushes the reactant ions into this part of the reaction chamber within the ring diaphragms (16), where they can react with the analyte molecules. By switching a DC voltage drop across the ring diaphragms (16) the analyte ions formed can later be pushed into the ion funnel (5).

Figure 5:
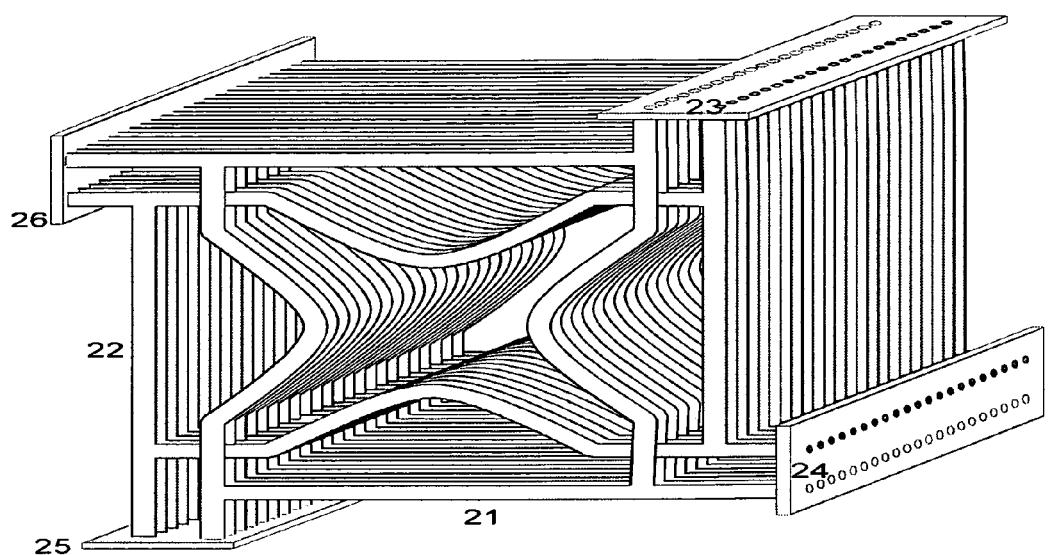

FIG. 5 represents a section of a quadrupole diaphragm stack. This diaphragm stack forms the section (6) in the FIGS. 1 to 4.

Figure 6:
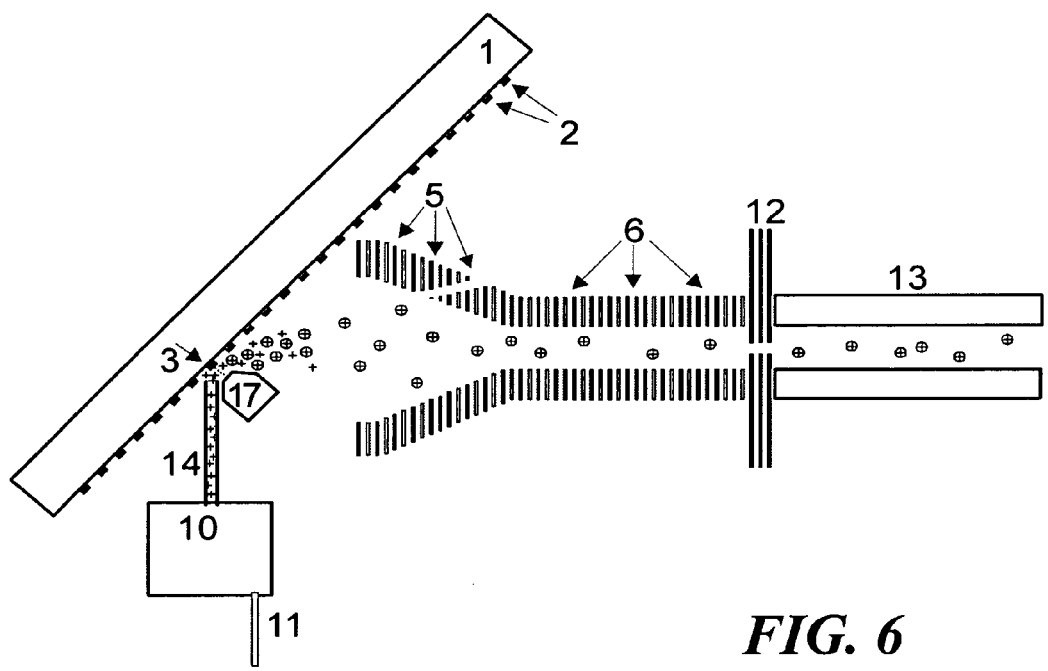

FIG. 6 shows an instrument for continuous desorption. A laser diode (17) with integrated focusing and integrated deflection mirror sweeps the sample (3) with a desorbing beam of light in an oscillating motion; the sample support plate (1) also moves accordingly in order to obtain continuous desorption of the analyte molecules. A stream of ambient gas with reactant ions is continuously blown out of the reactant ion source (10) through the tubular ion guide (14) to the sample (3).

Figure 7:
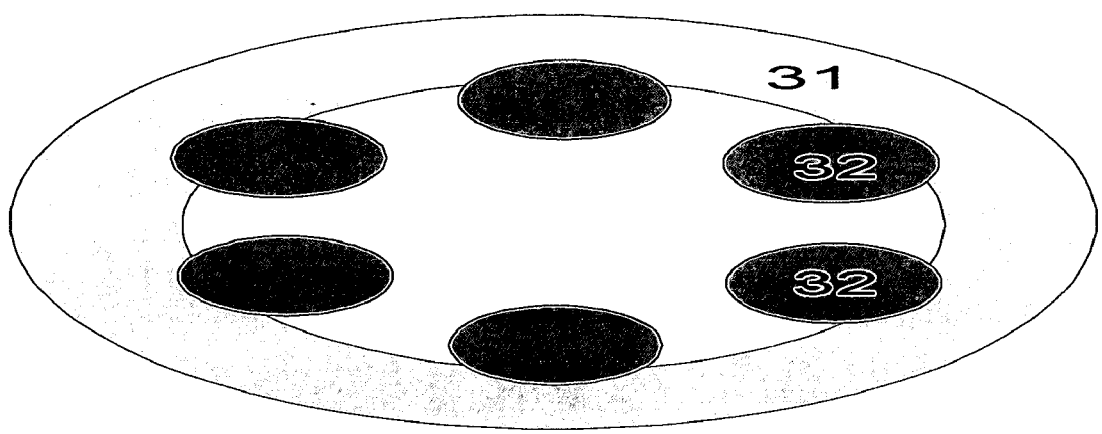

FIG. 7 represents a tubular ion guide which can be used to supply the reactant ions together with ambient gas by virtue of the casing (31) of the hexapole rods (32).

DETAILED DESCRIPTION

Some embodiments of methods, ion sources for generating analyte ions from desorbed analyte molecules, and associated spectrometers are presented in the claims 1 to 19.

A first favorable embodiment of an instrument, which operates with pulsed laser light, and a corresponding method, is illustrated here using FIGS. 1 to 3. These illustrations represent three consecutive method phases in one pulse cycle of the method.

A sample support plate (1) carries a large number of samples (2). The sample support plate can be made of any material; it is favorable, however, if a metallic core, a metallic backing or a metallic surface can carry an electric potential which can be used for a subsequent acceleration of the ions. Moreover, the sample support plate (1) must be made in such a way that the samples (2) are firmly held and can later be desorbed without larger lumps of sample breaking off. Since, for the favorable embodiment described here, the desorption is carried out using laser light, the surface of the sample support plate must be reasonably resistant to ablation by the pulse of laser light. Parallel to the surface which holds the samples (2), the sample support plate (1) can be transposed in two directions so that all the samples (2) in succession can be brought into the focus of the beam of laser light (9). In FIG. 1, the specially labeled sample (3) is at the focus of the beam of laser light (9).

With normal UHV MALDI, the MALDI samples consist of a matrix substance with a low proportion of analyte molecules, only around one hundredth of one percent. The dilution means that the analyte molecules are not desorbed in the form of dimers or trimers; this is because once formed, dimers and trimers usually will not separate again in the gaseous phase. In this embodiment, the samples (2, 3) can be made exactly the same as for UHV MALDI. The low proportions of analyte ions which are formed during the laser desorption of such preparations amount to only a very small proportion of the analyte ions formed downstream. The matrix substance used in this invention basically therefore does not have to perform the ionization at all; it is therefore possible to use quite different, and especially non-ionizing, matrix substances. The functions of the matrix substance therefore consist only in holding the analyte molecules firmly in a finely distributed form on the sample support plate (1), absorbing laser light out of the light pulse (9) and desorbing the sample material in such a way that the analyte molecules can be transferred into the gaseous form largely undamaged and individually. A special form of the matrix substances, which decomposes into small molecules when subjected to laser light, is discussed below. In fact, the samples do not have to contain a matrix substance; adsorbed analyte molecules can also be desorbed naked from the surface of a suitable sample support plate, as is familiar from laser desorption (LD), where it was frequently used.

A small fraction of the sample (3) is now desorbed in the focus of the laser beam (9), the laser beam (9) from the laser (8) being deflected via the mirror (7) onto the sample (3). The lenses required for focusing are not shown in FIG. 1. In this embodiment, the laser (8) is a pulsed laser; the desorption is a pulsed desorption, which generates its own desorption vapor cloud. For the matrix substances of conventional UHV MALDI, a UV laser in the wavelength range roughly between 320 and 360 nanometers is used; this can also be used here for similar sample preparations. Depending on the absorption characteristics of the matrix substance, it is also possible to use light of another wavelength range here, for example light from an IR laser. The pulse length of the laser is not so important here; it is possible to use lasers with pulse lengths between several hundred femtoseconds and several microseconds. Inexpensive UV lasers supply pulse lengths of between 2 and 10 nanoseconds.

The sample (3) and the focus of the beam of laser light (9) are located at the entrance aperture of a reaction chamber (15) which is formed from a large number of enclosing ring diaphragms (4) and (5), whose internal apertures form a virtual wall for ions in the reaction chamber. The ring diaphragms are supplied with an RF voltage, the two phases of the RF voltage each being applied across alternate adjacent ring diaphragms. This forms a so-called pseudopotential in front of the virtual wall of the reaction chamber which repels ions of both polarities and can thus confine them in the reaction chamber (15). The ring diaphragms can be separated by open spaces, in which case the desorption cloud eventually escapes through these open spaces. The reaction chamber can also have an impenetrable wall, however, so that the desorption cloud is detained for a long time, for example for very efficient reactions with the reactant ions. The ring diaphragms can then be printed on the wall of the reaction chamber with a conductive paint, for example.

This reaction chamber and its environment are filled with an ambient gas, preferably ultrapure nitrogen. This ambient gas can be adjusted to a favorable pressure in the region of around 30 to 300 Pascal, the optimum pressure being distinguished by optimum ionization of the analyte molecules. This optimum pressure can also lie slightly outside this stated pressure range and be in the region between 10 and 1,000 Pascal.

FIG. 1 shows this reaction chamber (15) at the time of the laser bombardment, i.e., at the time that the beam of laser light (9) is incident on the sample (3). At this time, the reaction chamber (15) is not only filled with ambient gas but, in particular, also with reactant ions which originate from the reactant ion source (10). The reactant ions, which are generated in the interior of the reactant ion source (10), can be guided via a small ion guide (14) into the reaction chamber (15). The ion guide leads into the apertured diaphragm system of the ion funnel (5), which forms a part of the reaction chamber (15). The ion guide can be designed as a quadrupole rod system or as a hexapole rod system, for example. How such ion guides join the ring diaphragm systems is described in the patent application publication DE 10 2004 028 419.9. The systems of apertured diaphragms (4, 5) of the reaction chamber (15), which likewise form an ion guide, lead the reactant ions further in the direction of the desorption point in front of the sample (3).

Some $10^6$ to $10^8$ reactant ions can be stored, depending on the size of the reaction chamber (15). For a reaction chamber with an internal diameter of around 30 millimeters and approx. 80 millimeters in length, more than $10^7$ reactant ions can be collected; the reactant ions are then, however, repelled by their own space charge so that they are then predominantly located at the virtual wall of the reaction chamber, where they form a layer. It is sometimes better to operate with a filling of only about $10^5$ reactant ions, which can be made available by a good reactant ion source in several tens of microseconds. A good reactant ion source can easily supply an ion current of around one nanoampere, i.e., around $10^{10}$ ions per second.

In the reactant ion source (10), molecules of a favorable gas mixture, for example propane, butane or pentane in slightly moist ultrapure nitrogen, are transformed into reactant ions by a reaction chain. The gas mixture is introduced through the gas feeder (11) into the reactant ion source. The ion source contains, as conventional CI sources do, thermionic cathodes and acceleration diaphragms to generate an electron beam, which is guided by the magnetic field of two permanent magnets. The reaction chain begins with an ionization of the predominating ultrapure nitrogen by electron collision; water complex ions are then very rapidly formed and the reaction chain finally finishes with the formation of the reactant ions. For example, with butane ($C_4H_{10}$) as the main constituent of the mixture, the reactant ions formed are predominantly of the form $C_4H_{11}^+$ (protonated butane) and $C_4H_9^+$ (protonated butene). These are eminently suitable for the protonation of analyte molecules of higher molecular weights above around 80 atomic mass units. These reactant ions are especially good at protonating tryptic digest peptides, a particularly common analytical task. The reactant ions are transferred within this ion source (10) by special devices, for example a mini-ion funnel, into the ion guide (14) which guides the reactant ions to the desorption point or to the reaction chamber. In the simplest case, the reactant ions are blown by the gas mixture through the ion guide (14).

It is also possible to generate completely different types of reactant ions, for example ions having molecular weights of several hundred atomic mass units but which nevertheless ionize peptides and proteins well. Partially fluorinated alkanes, for example, are suitable for this, but there are many substance groups which can be used here. The unused reactant ions of this high mass type can be transmitted together with the analyte ions after their ionization for a subsequent post-ionization of the analyte ions with one or more additional protons, for example.

FIG. 2 shows the state some 50 microseconds after the laser bombardment. A vaporization cloud (16) has formed which has expanded adiabatically into the ambient gas because of its very high initial pressure. Owing to the low ambient pressure and the relatively long free path length between the collisions, at least some of the cloud (16) with vaporized sample material mixes immediately with the ambient gas and the reactant ions contained therein. There is therefore a high reaction probability of the analyte molecules being protonated to analyte ions in collisions with the reactant ions.

Despite relatively rapid mixing, part of the ambient gas including the reactant ions is pushed along by the vaporization cloud (16) in front of it. The reaction chamber is shown in FIGS. 1 to 3 with an open system of ring diaphragms. The molecules of the vaporization cloud can then finally leave the reaction chamber through the spaces between the ring diaphragms, but not the ions. The reactant ions of the receding part of the ambient gas are initially held up at the pseudopotential of the virtual wall; they form a relatively dense layer. This layer means that a large proportion of the remaining analyte molecules are protonated by reactions. The analyte ions are also kept confined by the virtual wall of the pseudopotential.

In a closed reaction chamber, the processes proceed in basically the same way. While the desorption cloud here cannot escape through the spaces of the ring diaphragms, the non-ionized analyte molecules can, if they diffuse as far as the walls and condense on the walls of the reaction chamber, a process which likewise brings about a removal of the analyte molecules.

It is quite possible for the yield of analyte ions to be 10 percent of the free analyte molecules and more if the reaction chamber is well designed and the ambient gas has the optimal pressure. When using a matrix substance which does not form splashes of molten matrix material or broken off lumps, it is thus possible to obtain a very high yield of analyte ions. Molten splashes or solid lumps broken off by explosion can confine considerable quantities of analyte molecules and remove them from the sample so that these analyte molecules are excluded from ionization.

FIG. 3 illustrates how the analyte ions are now driven as a cloud (17) into the funnel-shaped part (5) of the reaction chamber, and from there into the quadrupole diaphragm stack (6), by a slight DC voltage gradient of a few volts across the ring diaphragm systems (4) and (5), said voltage gradient being superimposed on the RF voltages. During this process, the RF voltage across the ring diaphragm systems (4), (5) and (6) can also be increased, driving the low mass reactant ions, which are then below the mass threshold to keep the ions stably in the reaction chamber, out of the reaction chamber either through the spaces between the apertured diaphragms or by colliding with the ring-shaped apertured diaphragms.

This filtering out of the low mass reactant ions is particularly successful if carried out in the quadrupole part (6) of the diaphragm stack. In this quadrupole diaphragm stack (6) there is not only a slight DC voltage drop but also a quadrupole RF field which brings the analyte ions, whose motion is damped in the ambient gas, into the axis of the diaphragm stack (6), from where they can be very effectively transmitted through the apertured diaphragm lens (12) into an RF ion guide (13). In well-designed reaction chambers, the transfer of the analyte ions from the reaction chamber into the downstream ion guide (13) can be done in around 50 microseconds.

The quadrupole RF field has a very sharply defined lower stability limit for the mass of the ions, and therefore rejects ions of low mass.

This type of quadrupole diaphragm stack is shown in FIG. 5. It consists of diaphragms (21, 22) of the same shape, which are arranged one behind the other and rotated through 90° with respect to each other, and which can be individually supplied with DC potentials as well as both being supplied together with RF gradient along the axis onto the quadrupole RF voltage.

The maximum pulse frequency for this pulsed desorption mode is also obtained from the duration for the individual phases within a pulse cycle. Since the expansion of the desorption cloud with the reaction of the analyte molecules with the reactant ions takes around 50 microseconds, and the expulsion of the analyte ions formed likewise takes around 50 microseconds, the maximum pulse frequency is around 10 kilohertz. This does not yet take into account the fact that the reaction chamber has to be refilled with reactant ions. This filling process can be very short if the reactant ion source is very good and little filling is required. For a good yield of analyte ions it is more favorable, however, to fill a very large number of reactant ions, a process which will then take more like 100 microseconds or longer. The maximum pulse frequency is then around 5 kilohertz. For UHV MALDI, frequencies between 20 hertz and around 2 kilohertz are used hitherto.

The ion guide (13), which serves here to collect the analyte ions from the ion source according to the invention, is shown here simply as one example of a system which can collect, if necessary transmit or temporarily store the analyte ions for a time. As illustrated in FIG. 3, the ion guide can consist of pole rods supplied with RF voltage. It can, but does not have to, transmit the analyte ions into the analyzer part of the mass spectrometer, where they are analyzed according to their mass and intensity. In place of a mass spectrometer, any other suitable type of spectrometer can be used for the analysis of the analyte ions, for example an ion mobility spectrometer, or an optical spectrometer.

Another favorable embodiment, but one which likewise operates with pulsed laser light, has a reaction chamber which is not completely surrounded by a pseudopotential, as is shown in FIG. 4. It is quite possible for one part of the reaction chamber to be surrounded by a real DC potential, for example in the form of rings (16) which are at a DC potential. When combined with the same potential across the sample support plate (1) they form a potential well into which the reactant ions can be pushed by a suitable mid potential across the ion funnel (5), as illustrated in FIG. 4. After the analyte ions have been generated, a voltage drop from the sample support plate to the ion funnel can be switched on across the DC rings; this voltage drop drives the analyte ions into the ion funnel. Several embodiments are thus possible, but all follow the same basic idea of the invention.

As already noted above, the conventional matrix substances and methods of preparation can be used for the preparation of the samples (2). For example, the samples can be applied in dissolved form with pipetting robots to the sample support plate, where they are dried. Particularly hydrophilic regions on the sample support plate in a hydrophobic environment can limit the crystallization of the samples to these hydrophilic regions. A large number of matrix substances are known which are each optimal for certain groups of analyte substances which they ionize particularly well.

Since it hardly matters in this invention whether the laser desorption already supplies analyte ions or not, it is also possible to use matrix substances for the laser desorption which do not protonate. Matrix substances which decompose on desorption, forming gaseous molecules of the type $CO_2$, $H_2O$ and $N_2$, as already explained in DE 196 08 963 for MALDI at atmospheric pressure, can be particularly favorable. This decomposition occurs with many explosives, but other substance groups can also be so unstable that they decompose during the brief heating up in the laser bombardment. A matrix substance which is particularly favorable for this purpose is cellulose dinitrate (frequently called dinitrocellulose), for example. This substance is especially good at binding peptides and proteins to its surface. When applied as an open-pored foam to sample support plates, it has a very large absorbing surface; the solutions with analyte substances can then be applied directly onto these foam spots. When subjected to laser bombardment, the only points which decompose are those directly in the focus of the laser light; the whole sample coating does not explode.

A second favorable embodiment of the method and instrument does not begin with a pulsed desorption of the analyte molecules, but with a continuous one, as illustrated in FIG. 6. Modern laser diodes as used in CD or DVD players are suitable here, for example. With focusing lens and deflecting micromirror, the laser diode can be integrated to a very small unit (17) which can be placed close to the samples to be desorbed, here in front of the sample (3). These laser diodes, which are available for various wavelengths from infrared and visible through to ultraviolet light, are special because they are able to produce a very fine focus. The focus diameter is roughly proportional to the wavelength and amounts to fractions of a micrometer. In the focus there is an energy density which can change material, for example melting it, even at high scan speeds as is familiar from CDs.

These diodes are suitable for continuously desorbing adsorbed analyte molecules in their focus, which should preferably be moved very quickly over the sample support (1). The high speed of the focus on the sample support plate (1) ensures that there is no localized overheating of the sample support (1) or the sample to be desorbed (3). For a very small focus, the focal length must be kept very small, but it is also possible to achieve sufficiently small focal diameters for the desorption with separations of several millimeters. A high focus speed on the sample support in the order of 0.1 to 10 meters per second can be achieved by a combined movement of the laser beam from the laser diode by means of an integrated oscillating micromirror, on the one hand, and a moderately fast movement of the sample support (1) on the other; it is favorable if the two movements are allowed to run at right angles to each other. Speeds in the range between 0.01 and 1 meter per second can also be achieved by movement of the sample support alone.

Since the wavelength of the desorbing light is not necessarily critical, it is also possible to use a light emitting diode (LED). These can transmit light of various single wavelengths, and also a mixture of wavelengths. It is also possible to achieve good focusing of the light to a beam with lenses of short focal lengths.

Continuous desorption is also achieved when a laser diode is modulated with a very high modulation frequency. The modulation can be sinusoidal or square, and the ratio of emission intervals to rest intervals can be adjustable, for example. A modulation frequency of larger than 20 kilohertz generates a continuous current of desorbed analyte molecules because the individual vaporization clouds continuously merge with one another. Furthermore, research into UHV MALDI has shown that evaporation continues for some time (possibly many microseconds) after the laser bombardment, but now practically without ion formation. Particularly favorable here are modulation frequencies of the laser diodes of a hundred kilohertz up to ten megahertz, especially if a decomposable matrix is used.

The desorption of the analyte molecules as a result of this rapidly moving laser diode focus is particularly successful if the analyte molecules are adsorbed naked on a suitable sample support. They therefore do not necessarily have to be embedded into a matrix substance.

A particularly favorable preparation of the samples with a matrix substance for this continuous desorption consists in adsorbing the analyte molecules on a very thin layer of explosive or other decomposable material. Eminently suitable is a thin layer of cellulose dinitrate only one micrometer thick which is applied as a thin lacquer film to the sample locations to subsequently hold the analyte molecules, for example. When dissolved in acetone, cellulose dinitrate forms a lacquer which can be worked very well. This type of lacquer with relatively low nitrated cellulose is commercially available as "boat varnish", but it does not have a high degree of purity. This thin layer can be loaded well with peptides or proteins, since the layer of lacquer is extraordinarily affine towards these substances. A square millimeter of lacquer can hold up to a picomole of analyte substances. The spots of lacquer designated for the samples can be one square millimeter, or even 10 or 50 square millimeters in size. If the spots are 7×7 millimeters, it is quite possible to accommodate 96 samples on a sample support plate the size of a microtitration plate; with 3×3 millimeter spots, 384 samples can be accommodated.

The thin layer of explosive continuously decomposes in the focus of the laser diode, the adsorbed analyte molecules also being blown into the ambient gas. Here, they are protonated by the reactant ions fed in either continuously or in pulses. The explosive decomposes into water, carbon dioxide and nitrogen, i.e., it forms no molecules of medium weight, unlike the matrix materials customarily used. This means that interfering background ions, one of the disadvantages of UHV MALDI, are not formed. The analyte ions are then preferably continuously drawn by electric DC potentials into the ion funnel (5), from where they are transmitted into the ion guide (13) via the quadrupole diaphragm stack (6) and the arrangement of lenses (12). Particularly favorable for this decomposition of thin layers of explosive is a modulated laser diode with a modulation frequency of approx. 100 kilohertz to ten megahertz.

Instead of a thin layer of explosive it is also possible to again use a thin layer of open-pored explosive foam in order to obtain a larger surface for the adsorption of the analyte molecules. The open-pored foam can be obtained by rapid vacuum drying of lacquer spots which are soaked with water, for example.

For this method of continuous desorption the reactant ions from the reactant ion source can be blown by a narrow ion guide (14) directly to the desorption point. It is particularly favorable here if the ion guide is enclosed so as to be gas tight in order that the reactant ions can be blown directly to the desorption point in a current of ambient gas. A tubular ion guide of this type with an enclosed hexapole rod system is shown in FIG. 7 in cross section. The ion guide (14) can be manufactured with an external diameter of only some two to three millimeters. The ambient gas blown in means that the desorbed analyte molecules and other desorption vapors are also blown across and away from the desorption point. This is favorable not only for efficient reactions between analyte molecules and reactant ions, but also for keeping clean the focusing lenses or micromirror of the systems of laser diodes (17).

In the description of the method according to the invention, a protonation of the analyte molecules was sometimes referred to, a process which naturally leads to positive analyte ions. Similarly, the analyte molecules can also be transformed into negatively charged analyte ions, however, by reactions with corresponding negative reactant ions. This requires deprotonating reactions or also electron transfer reactions. Therefore on no account should the reaction to negatively charged analyte ions be excluded; on the contrary, with this invention they should be expressly included.

Applications of the invention are for ion sources in mass spectrometers of various types and also for other types of spectrometers, for example ion mobility spectrometers. Of particular interest is an application as a highly sensitive ion source in a tandem mass spectrometer which contains a time-of-flight mass analyzer with orthogonal ion injection (OTOF) as the analyzer, for example. This type of mass analyzer has maximum sensitivity, large dynamic measuring range, and an outstanding mass accuracy. The fragmentation unit can be either a collision cell or any other fragmentation stage. Since the fragmentation of biopolymers works best when starting with doubly charged ions, a device for protonating the singly charged ions generated here can be interposed.

This example is only one of many, however. It would also be possible to list additional spectrometric applications here. With knowledge of this invention, the specialist can create further obvious embodiments and applications but ones which will always be governed by the basic idea of the invention and hence the scope of protection.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for the generation of analyte ions from analyte molecules for an analysis in a spectrometer, comprising the steps of:
    (a) providing the analyte molecules in a sample on a solid sample support within a gas at a pressure between 10 and 1,000 Pascal,
    (b) generating reactant ions in a reactant ion source,
    (c) feeding the reactant ions to a space in front of the sample, and
    (d) desorbing the analyte molecules from the sample, thereby ionizing the desorbed analyte molecules by the reactant ions.

2. The method according to claim 1, wherein the desorption of the analyte molecules is carried out continuously.

3. The method according to claim 2, wherein the continuous desorption of the analyte molecules is carried out by means of a continuous beam of light from one of a laser, a laser diode or a light-emitting diode.

4. The method according to claim 2, wherein the continuous desorption of the analyte molecules is carried out by means of a high frequency modulated beam of light from one of a laser, a laser diode or a light-emitting diode with a modulation frequency greater than 20 kilohertz.

5. The method according to claim 1, wherein the desorption of the analyte molecules is carried out in pulses with a pulse frequency of less than ten kilohertz.

6. The method according to claim 5, wherein the desorption is carried out by pulses of laser light from a pulsed laser.

7. The method according to claim 1, wherein the analyte molecules are adsorbed on the sample support without additives.

8. The method according to claim 1, wherein the analyte molecules are located on the sample support surrounded by matrix molecules.

9. The method according to claim 8, wherein the analyte molecules are located on the sample support surrounded by matrix molecules which decompose during the desorption.

10. The method according to claim 1, wherein the reactant ion source for the generation of the reactant ions comprises a chemical ionization source wherein the reactions between the reactant ions and the analyte molecules occur outside the reactant ion source.

11. The method according to claim 10, wherein the reactant ion source operates at substantially the same pressure as that at which the desorption occurs.

12. The method according to claim 1, further comprising the step of collecting analyte ions formed in step (d) by an ion funnel in front of the sample support and transmitting the analyte ions to another location.

13. The method according to claim 1, wherein the desorption of the analyte molecules in step (d) is carried out at an ambient gas pressure of between 30 and 300 Pascal.

14. An ion source for the ionization of analyte molecules located in samples on a sample support, comprising a) a vacuum chamber with a gas at a pressure between 10 and 1,000 Pascal to accommodate the sample support,
b) a desorption device operable to desorb the analyte molecules of a sample on the sample support,
c) a source of reactant ions for the generation of reactant ions, and
d) an ion guide for guiding the reactant ions from the source of the reactant ions to the space in front of the sample.

15. The ion source according to claim 14, wherein analyte ions are formed by a reaction of the analyte molecules and the reactant ions and wherein the ion source further comprises an ion funnel for the collection of the analyte ions and the transmittance of collected ions to another location.

16. The ion source according to claim 14, wherein the desorption device comprises one of a laser, a laser diode or a light-emitting diode.

17. The ion source according to claim 14 further comprising a spectrometer coupled to the ion source.

18. The ion source according to claim 17, wherein the spectrometer is a mass spectrometer.

19. The ion source according to claim 17, wherein the spectrometer is an ion mobility spectrometer.

* * * * *